Feb. 5, 1957 E. H. DOERR Plant Pat. 1,561
WHITE GLADIOLUS PLANT
Filed Feb. 2, 1956
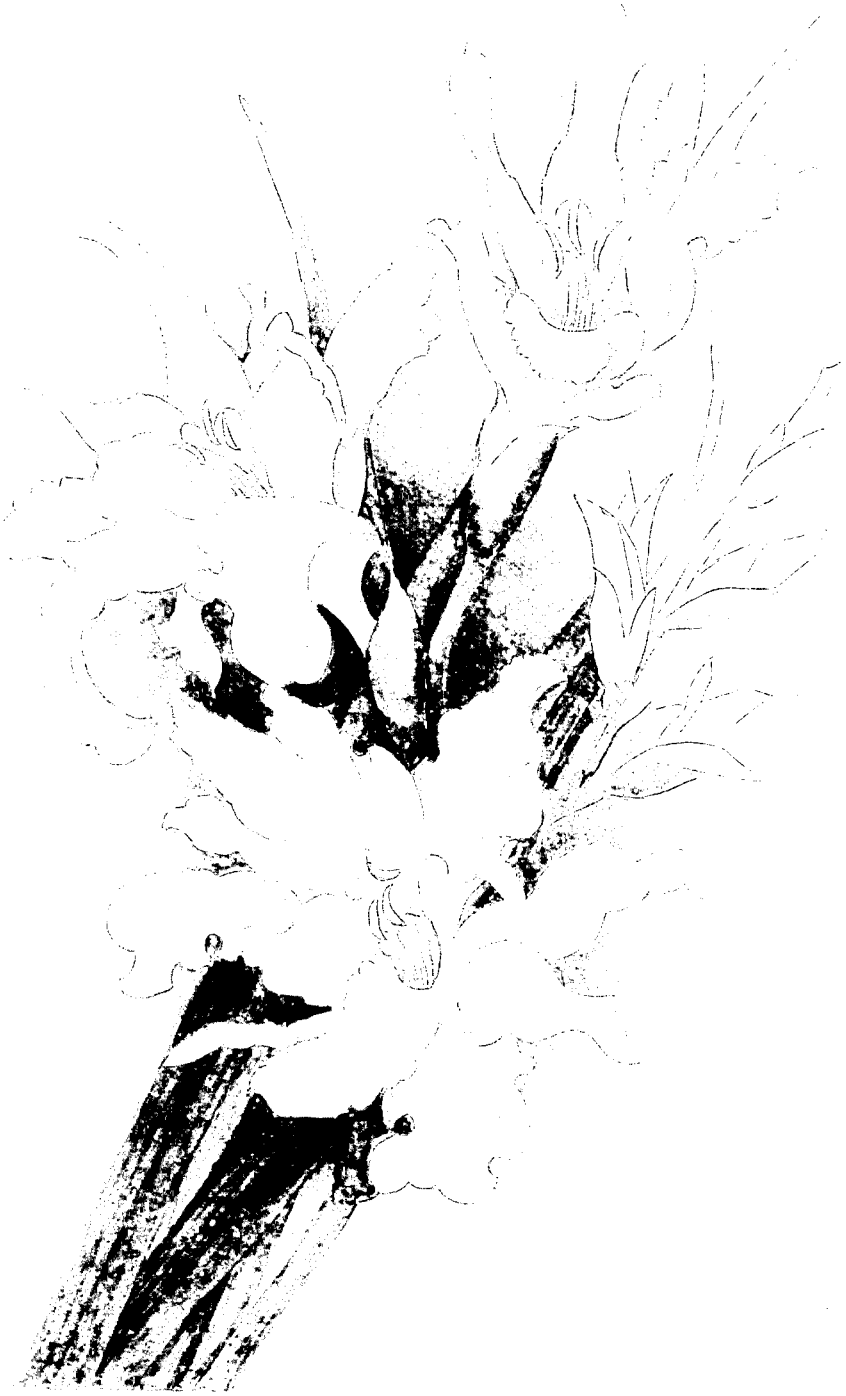
WITNESS
Addison E. Avery
INVENTOR
ERVIN H. DOERR
by Rummler, Rummler & Snow
ATTYS.

United States Patent Office

Plant Pat. 1,561
Patented Feb. 5, 1957

1,561

WHITE GLADIOLUS PLANT

Ervin H. Doerr, New Ulm, Minn.

Application February 2, 1956, Serial No. 563,159

1 Claim. (Cl. 47—60)

My present invention concerns a new and improved variety of white gladiolus plant which originated as a seedling from a cross made by me, at my nursery in New Ulm, Minnesota, between the unpatented varieties "Wedgwood" (Fischer), as the seed parent, and "Multipetal #1," as the pollen parent.

This new variety has been asexually reproduced by me, at New Ulm, Minnesota, and increased from cormels produced by mature bulbs through several generations and its characteristics appear to be permanently fixed. I have identified this new variety as "Seedling #920-3."

This new variety of gladiolus is the result of prolonged breeding efforts—extending over a period of fifteen years—to produce a white gladiolus. The result is an unusual white flower, not merely of an off-white shade, but having a beautiful cream tone with a very light touch of green in the throat and at base of the floret.

Another distinctive characteristic of this new variety is the pale green coloring of the new buds which gradually turns to a delicate tone of yellow, as the buds mature, and then, as the petals unfurl becomes the exquisite pale cream of the fully opened flower.

Another striking feature of this new variety resides in the long lacy serrated petals—which number 8 or more to the floret—each having a delicate green stripe at its base which becomes darker in the throat of the floret.

One of the conspicuous characteristics of the new plant is the curving downward of the spikes during summer heat and the raising of the heads again during cooler weather; thus giving an unusual form to the spikes and making more adaptable to easy arrangement in floral work. Also the form of the florets and petals provides a soft willowy spray which lends itself more gracefully to floral arrangement, either alone or with other flowers.

The accompanying painting shows a spray of the new gladiolus plant in its natural colors with the flowers in the different stages of development.

The following is a detailed description of my new variety.

Parentage: Seedling.
- *Seed parent.*—"Wedgwood" (Fischer).
- *Pollen parent.*—"Multipetal #1."

Flower:
- *Blooms.*—Once. Early in season.
- *Size.*—Medium to small.

- *Petalage.*—8 or more to each floret.
  - *Petaloids.*—None.
- *Form.*—Long, lacy and serrated.
- *Color.*—Outer petals, cream with light touch of green in throat or floret and on base of each petal.
  - *Reverse side.*—Same as inside.
  - *Discoloration.*—None.
- *Texture.*—Soft.
- *Appearance.*—Satiny.
- *Lasting quality.*—On plant—fair. As a cut flower—fair.

Bud:
- *Size.*—Average.
- *Form.*—Average long.
- *Color.*—When sepals first divide—Pale green to yellow. When sepals begin to unfurl—Yellow cream turning to cream at tips.

Plant:
- *Height.*—24 inches.
- *Growth.*—Normal and healthy.

Genital organs:
- *Stamens, anthers.*—Normal.
  - *Length.*—Average.
  - *Number.*—3.
  - *Color.*—Cream.
  - *Arrangement.*—Normal.
  - *Pollen.*—Cream color.
- *Styles.*—Number 1 to several, single stigma on each.
- *Ovaries.*—Abnormal.

The color designations according to "A Dictionary of Color" by Maerz and Paul, and "Horticultural Colour Chart" by The British Colour Council are as follows:

| | Plate | Letter | No. |
|---|---|---|---|
| Flower (Hort. Colour Chart): White to very pale creamy White. | 121 | -------- | 493/3 minus. |
| Stamens: White stem—Tip | 9 | D | 3. |
| Pistils: All White | 9 | A | 1. |
| Throat: Pale green | 17 | G | 4. |
| Buds: (Maerz and Paul) | 17 | L | 3. |
| To (Hort. Colour Chart) Dresden Yellow. | 64 | To | 64 to 64/2. |
| Leaves: Green (Maerz and Paul) | 21 | J | 8. |

The soft, satiny texture, distinctive creamy white coloring, the large number of long, lacy, serrated petals, and the willowy feature of the spray, combine to enhance the value of this plant as a commercial product.

Having thus disclosed my invention, I claim:

A new and distinct variety of gladiolus plant, substantially as shown and described, characterized by its flower having long, serrated and lacy, creamy white petals, the delicate shade of green at the base of the petals and in the throat of the florets, the pale green color of the buds when the sepals first begin to divide, and the light yellow color of the new petals as the sepals begin to unfurl which turns to creamy white in the opened floret.

No references cited.